(12) United States Patent
Mayfield et al.

(10) Patent No.: US 10,182,887 B2
(45) Date of Patent: *Jan. 22, 2019

(54) TITANIUM NANO-SCALE ETCHING ON AN IMPLANT SURFACE

(71) Applicant: BIOMET 3I, LLC, Palm Beach Gardens, FL (US)

(72) Inventors: Robert L Mayfield, Jupiter, FL (US); Ross W Towse, San Marcos, CA (US)

(73) Assignee: Biomet 3I, LLC, Palm Beach Gardens, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/696,965

(22) Filed: Sep. 6, 2017

(65) Prior Publication Data

US 2017/0360532 A1    Dec. 21, 2017

Related U.S. Application Data

(63) Continuation of application No. 15/066,213, filed on Mar. 10, 2016, now Pat. No. 9,757,212, which is a
(Continued)

(51) Int. Cl.
*A61C 8/00* (2006.01)
*C23F 1/30* (2006.01)
(Continued)

(52) U.S. Cl.
CPC .............. *A61C 8/0015* (2013.01); *A61C 8/00* (2013.01); *A61C 8/0012* (2013.01);
(Continued)

(58) Field of Classification Search
CPC ....... A61C 8/00; A61C 8/0015; A61C 8/0012; A61C 8/0013; A61C 8/0022;
(Continued)

(56) References Cited

U.S. PATENT DOCUMENTS

| 3,603,288 A | 9/1971 | Case et al. |
| 3,772,355 A | 11/1973 | Merz |

(Continued)

FOREIGN PATENT DOCUMENTS

| AU | 6220565 A | 2/1967 |
| AU | 6227170 A1 | 9/2006 |

(Continued)

OTHER PUBLICATIONS

"U.S. Appl. No. 13/074,670, Final Office Action dated Aug. 6, 2013", 9 pgs.
(Continued)

*Primary Examiner* — Duy Vu N Deo
(74) *Attorney, Agent, or Firm* — Schwegman Lundberg & Woessner, P.A.

(57) ABSTRACT

A method of forming an implant to be implanted into living bone is disclosed. The method comprises the act of roughening at least a portion of the implant surface to produce a microscale roughened surface. The method further comprises the act of immersing the microscale roughened surface into a solution containing hydrogen peroxide and a basic solution to produce a nanoscale roughened surface consisting of ranopitting superimposed on the microscale roughened surface. The nanoscale roughened surface has a property that promotes osseointegration.

20 Claims, 11 Drawing Sheets

Related U.S. Application Data continuation of application No. 14/687,625, filed on Apr. 15, 2015, now Pat. No. 9,283,056, which is a continuation of application No. 14/049,961, filed on Oct. 9, 2013, now Pat. No. 9,034,201, which is a continuation of application No. 13/074,670, filed on Mar. 29, 2011, now Pat. No. 8,641,418.

(60) Provisional application No. 61/318,641, filed on Mar. 29, 2010.

(51) Int. Cl.
| | | |
|---|---|---|
| C23F 1/00 | (2006.01) | |
| A61L 27/04 | (2006.01) | |
| B82Y 30/00 | (2011.01) | |
| C23F 1/26 | (2006.01) | |
| C23F 1/38 | (2006.01) | |
| C23G 1/10 | (2006.01) | |
| A61C 13/00 | (2006.01) | |

(52) U.S. Cl.
CPC .......... *A61C 8/0013* (2013.01); *A61C 8/0022* (2013.01); *A61C 8/0037* (2013.01); *A61C 13/00* (2013.01); *A61L 27/04* (2013.01); *B82Y 30/00* (2013.01); *C23F 1/00* (2013.01); *C23F 1/26* (2013.01); *C23F 1/30* (2013.01); *C23F 1/38* (2013.01); *C23G 1/106* (2013.01); *A61C 2008/0046* (2013.01); *A61L 2400/18* (2013.01)

(58) Field of Classification Search
CPC ....... A61C 8/0037; A61C 13/00; A61L 27/04; B82Y 30/00; C23F 1/00; C23F 1/26; C23F 1/30; C23F 1/38; C23F 1/106
See application file for complete search history.

(56) References Cited

U.S. PATENT DOCUMENTS

| | | |
|---|---|---|
| 3,984,914 A | 10/1976 | Schwartz |
| 4,097,935 A | 7/1978 | Jarcho |
| 4,131,597 A | 12/1978 | Bluethgen et al. |
| 4,145,764 A | 3/1979 | Suzuki et al. |
| 4,146,936 A | 4/1979 | Aoyagi et al. |
| 4,223,412 A | 9/1980 | Aoyagi et al. |
| 4,321,042 A | 3/1982 | Scheicher |
| 4,330,891 A | 5/1982 | Branemark et al. |
| 4,366,183 A | 12/1982 | Ghommidh et al. |
| 4,403,941 A | 9/1983 | Okiura et al. |
| 4,451,235 A | 5/1984 | Okuda et al. |
| 4,538,306 A | 9/1985 | Dorre et al. |
| 4,636,526 A | 1/1987 | Dorman et al. |
| 4,687,487 A | 8/1987 | Hintermann |
| 4,746,532 A | 5/1988 | Suzuki et al. |
| 4,818,559 A | 4/1989 | Hama et al. |
| 4,830,993 A | 5/1989 | Legrand et al. |
| 4,846,837 A | 7/1989 | Kurze et al. |
| 4,847,163 A | 7/1989 | Shimamune et al. |
| 4,863,474 A | 9/1989 | Brown et al. |
| 4,871,578 A | 10/1989 | Adam |
| 4,879,136 A | 11/1989 | Polz |
| 4,880,610 A | 11/1989 | Constantz |
| 4,882,196 A | 11/1989 | Shimamune et al. |
| 4,904,534 A | 2/1990 | Nagai |
| 4,908,030 A | 3/1990 | Linkow et al. |
| 4,909,846 A | 3/1990 | Barfurth et al. |
| 4,911,953 A | 3/1990 | Hosonuma et al. |
| 4,929,589 A | 5/1990 | Martin et al. |
| 4,944,754 A | 7/1990 | Linkow et al. |
| 4,960,646 A | 10/1990 | Shimamune et al. |
| 4,965,088 A | 10/1990 | Shimamune et al. |
| 4,988,362 A | 1/1991 | Toriyama et al. |
| 4,990,163 A | 2/1991 | Ducheyne et al. |
| 5,030,474 A | 7/1991 | Saita et al. |
| 5,068,122 A | 11/1991 | Kokubo et al. |
| 5,071,351 A | 12/1991 | Green, Jr. et al. |
| 5,071,434 A | 12/1991 | Tsuzuki et al. |
| 5,071,436 A | 12/1991 | Hue et al. |
| 5,077,132 A | 12/1991 | Maruno et al. |
| 5,092,890 A | 3/1992 | Pohlemann et al. |
| 5,128,169 A | 7/1992 | Saita et al. |
| 5,134,009 A | 7/1992 | Ichitsuka et al. |
| 5,141,576 A | 8/1992 | Shimamune et al. |
| 5,180,426 A | 1/1993 | Sumita |
| 5,185,208 A | 2/1993 | Yamashita et al. |
| 5,188,670 A | 2/1993 | Constantz |
| 5,196,201 A | 3/1993 | Larsson et al. |
| 5,205,921 A | 4/1993 | Shirkanzadeh |
| 5,219,361 A | 6/1993 | Von Recum et al. |
| 5,231,151 A | 7/1993 | Spencer et al. |
| 5,263,491 A | 11/1993 | Thornton |
| 5,279,720 A | 1/1994 | Divigalpitiya |
| 5,279,831 A | 1/1994 | Constantz et al. |
| 5,286,571 A | 2/1994 | Mirkin et al. |
| 5,344,457 A | 9/1994 | Pilliar et al. |
| 5,344,654 A | 9/1994 | Rueger et al. |
| 5,358,529 A | 10/1994 | Davidson |
| 5,364,522 A | 11/1994 | Wang |
| 5,397,642 A | 3/1995 | Li et al. |
| 5,456,723 A | 10/1995 | Steinemann |
| 5,478,237 A | 12/1995 | Ishizawa |
| 5,484,286 A | 1/1996 | Hansson |
| 5,501,706 A | 3/1996 | Arenberg |
| 5,522,893 A | 6/1996 | Chow et al. |
| 5,527,837 A | 6/1996 | Kondou et al. |
| 5,543,019 A | 8/1996 | Lee et al. |
| 5,558,517 A | 9/1996 | Shalaby et al. |
| 5,571,188 A | 11/1996 | Ellingsen |
| 5,580,429 A | 12/1996 | Chan et al. |
| 5,580,819 A | 12/1996 | Li et al. |
| 5,584,875 A | 12/1996 | Duhamel et al. |
| 5,603,338 A | 2/1997 | Beaty |
| 5,607,607 A | 3/1997 | Naiman et al. |
| 5,609,633 A | 3/1997 | Kokubo |
| 5,612,049 A | 3/1997 | Li et al. |
| 5,639,402 A | 6/1997 | Barlow et al. |
| 5,652,016 A | 7/1997 | Imura et al. |
| 5,700,289 A | 12/1997 | Breitbart et al. |
| 5,722,439 A | 3/1998 | Endelson |
| 5,726,524 A | 3/1998 | Debe |
| 5,730,598 A | 3/1998 | Story et al. |
| 5,733,564 A | 3/1998 | Lehtinen |
| 5,759,376 A | 6/1998 | Teller et al. |
| 5,759,598 A | 6/1998 | Gaier |
| 5,763,092 A | 6/1998 | Lee et al. |
| 5,766,247 A | 6/1998 | Aoki et al. |
| 5,766,669 A | 6/1998 | Pugh et al. |
| 5,767,032 A | 6/1998 | Hokkanen et al. |
| 5,772,439 A | 6/1998 | Yamaoka et al. |
| 5,807,430 A | 9/1998 | Zheng et al. |
| 5,811,151 A | 9/1998 | Hendriks et al. |
| 5,817,326 A | 10/1998 | Nastasi et al. |
| 5,858,318 A | 1/1999 | Luo |
| 5,871,547 A | 2/1999 | Abouaf et al. |
| 5,888,034 A | 3/1999 | Greenberg |
| 5,934,287 A | 8/1999 | Hyashi et al. |
| 5,947,893 A | 9/1999 | Agrawal et al. |
| 5,952,399 A | 9/1999 | Rentsch |
| 5,958,340 A | 9/1999 | Meyer |
| 5,958,504 A | 9/1999 | Lee et al. |
| 5,962,549 A | 10/1999 | Bonfield et al. |
| 5,981,619 A | 11/1999 | Shikinami et al. |
| 5,990,381 A | 11/1999 | Nishihara |
| 6,013,591 A | 1/2000 | Ying et al. |
| 6,051,272 A | 4/2000 | Stupp et al. |
| 6,069,295 A | 5/2000 | Leitao |
| 6,077,989 A | 6/2000 | Kandel et al. |
| 6,118,043 A | 9/2000 | Nies et al. |
| 6,129,928 A | 10/2000 | Sarangapani et al. |
| 6,136,369 A | 10/2000 | Leitao et al. |
| 6,139,585 A | 10/2000 | Li et al. |
| 6,143,037 A | 11/2000 | Goldstein et al. |
| 6,143,948 A | 11/2000 | Leitao et al. |

(56) References Cited

U.S. PATENT DOCUMENTS

| | | | |
|---|---|---|---|
| 6,146,686 A | 11/2000 | Leitao | |
| 6,146,767 A | 11/2000 | Schwartz | |
| 6,153,266 A | 11/2000 | Yokogawa et al. | |
| 6,153,664 A | 11/2000 | Wise et al. | |
| 6,183,255 B1 | 2/2001 | Oshida | |
| 6,190,412 B1 | 2/2001 | Lee et al. | |
| 6,200,137 B1 | 3/2001 | Holand et al. | |
| 6,206,598 B1 | 3/2001 | Johnson et al. | |
| 6,207,218 B1 | 3/2001 | Layrolle et al. | |
| 6,214,049 B1 | 4/2001 | Gayer et al. | |
| 6,221,111 B1 | 4/2001 | Piveteau et al. | |
| 6,261,322 B1 | 7/2001 | Despres, III et al. | |
| 6,270,347 B1 | 8/2001 | Webster et al. | |
| 6,280,474 B1 | 8/2001 | Cassidy et al. | |
| 6,280,789 B1 | 8/2001 | Rey et al. | |
| 6,280,863 B1 | 8/2001 | Frank et al. | |
| 6,290,982 B1 | 9/2001 | Seppala et al. | |
| 6,306,784 B1 | 10/2001 | Drescher et al. | |
| 6,306,925 B1 | 10/2001 | Clupper et al. | |
| 6,309,660 B1 | 10/2001 | Hsu et al. | |
| 6,338,810 B1 | 1/2002 | Carpena et al. | |
| 6,344,061 B1 | 2/2002 | Leitao et al. | |
| 6,344,209 B1 | 2/2002 | Saito et al. | |
| 6,344,276 B1 | 2/2002 | Lin et al. | |
| 6,372,354 B1 | 4/2002 | Park et al. | |
| 6,395,299 B1 | 5/2002 | Babich et al. | |
| 6,399,215 B1 | 6/2002 | Zhu et al. | |
| 6,419,708 B1 | 7/2002 | Hall et al. | |
| 6,426,114 B1 | 7/2002 | Troczynski et al. | |
| 6,428,803 B1 | 8/2002 | Ewers et al. | |
| 6,491,723 B1 | 12/2002 | Beaty | |
| 6,508,838 B2 | 1/2003 | Lee et al. | |
| 6,518,328 B2 | 2/2003 | Kumar | |
| 6,527,849 B2 | 3/2003 | Dry | |
| 6,527,938 B2 | 3/2003 | Bales et al. | |
| 6,530,958 B1 | 3/2003 | Cima et al. | |
| 6,544,732 B1 | 4/2003 | Chee et al. | |
| 6,569,292 B2 | 5/2003 | Coffer | |
| 6,569,489 B1 | 5/2003 | Li | |
| 6,589,365 B2 | 7/2003 | Ito | |
| 6,589,590 B2 | 7/2003 | Czernuszka et al. | |
| 6,596,338 B2 | 7/2003 | Scott et al. | |
| 6,617,142 B2 | 9/2003 | Keogh et al. | |
| 6,620,861 B1 | 9/2003 | Nakatuka et al. | |
| 6,645,644 B1 | 11/2003 | Schwartz et al. | |
| 6,652,765 B1 | 11/2003 | Beaty | |
| 6,689,170 B1 | 2/2004 | Larsson et al. | |
| 6,709,379 B1 | 3/2004 | Brandau et al. | |
| 6,733,503 B2 | 5/2004 | Layrolle et al. | |
| 6,740,366 B2 | 5/2004 | Hori et al. | |
| 6,790,455 B2 | 9/2004 | Chu et al. | |
| 6,812,471 B2 | 11/2004 | Popiolkowski et al. | |
| 6,853,075 B2 | 2/2005 | Auner et al. | |
| 6,919,070 B1 | 7/2005 | Rudin et al. | |
| 6,960,249 B2 | 11/2005 | Lin et al. | |
| 6,969,474 B2 | 11/2005 | Beaty | |
| 6,969,501 B2 | 11/2005 | Sapieszko et al. | |
| 6,991,803 B2 | 1/2006 | Sapieszko et al. | |
| 7,007,872 B2 | 3/2006 | Yadav et al. | |
| 7,018,418 B2 | 3/2006 | Amrich et al. | |
| 7,067,169 B2 | 6/2006 | Liu et al. | |
| 7,067,577 B2 | 6/2006 | Aramaki et al. | |
| 7,083,642 B2 | 8/2006 | Sirhan et al. | |
| 7,087,086 B2 | 8/2006 | Li et al. | |
| 7,105,030 B2 | 9/2006 | Despres, III et al. | |
| 7,112,063 B2 | 9/2006 | Bulard et al. | |
| 7,169,317 B2 | 1/2007 | Beaty | |
| 7,341,756 B2 | 3/2008 | Liu | |
| 8,641,418 B2* | 2/2014 | Mayfield | A61C 8/0012 433/173 |
| 9,034,201 B2* | 5/2015 | Mayfield | A61C 8/0012 216/102 |
| 9,283,056 B2 | 3/2016 | Mayfield et al. | |
| 9,757,212 B2 | 9/2017 | Mayfield et al. | |
| 2001/0020476 A1 | 9/2001 | Gan et al. | |
| 2002/0016635 A1 | 2/2002 | Despres, III et al. | |
| 2002/0018798 A1 | 2/2002 | Sewing et al. | |
| 2002/0028424 A1 | 3/2002 | Prestipino et al. | |
| 2002/0119325 A1 | 8/2002 | Park et al. | |
| 2002/0127391 A1 | 9/2002 | Kumar | |
| 2003/0005646 A1 | 1/2003 | Mchale, Jr. | |
| 2003/0082232 A1 | 5/2003 | Lee et al. | |
| 2003/0099762 A1 | 5/2003 | Zhang et al. | |
| 2003/0170378 A1 | 9/2003 | Wen et al. | |
| 2003/0175773 A1 | 9/2003 | Chee et al. | |
| 2003/0219466 A1 | 11/2003 | Kumta et al. | |
| 2003/0219562 A1 | 11/2003 | Rypacek et al. | |
| 2003/0231984 A1 | 12/2003 | Bright et al. | |
| 2004/0023048 A1 | 2/2004 | Schwartz et al. | |
| 2004/0024081 A1 | 2/2004 | Trieu et al. | |
| 2004/0053197 A1 | 3/2004 | Minevski et al. | |
| 2004/0053198 A1 | 3/2004 | Minevski et al. | |
| 2004/0053199 A1 | 3/2004 | Minevski et al. | |
| 2004/0121290 A1 | 6/2004 | Minevski et al. | |
| 2004/0121451 A1 | 6/2004 | Moritz et al. | |
| 2004/0145053 A1 | 7/2004 | Auner et al. | |
| 2004/0149586 A1 | 8/2004 | Sul | |
| 2004/0153165 A1 | 8/2004 | Li et al. | |
| 2004/0210309 A1 | 10/2004 | Denzer et al. | |
| 2004/0214326 A1 | 10/2004 | Cousins et al. | |
| 2004/0234604 A1 | 11/2004 | Mecking et al. | |
| 2004/0241613 A1 | 12/2004 | Jansen et al. | |
| 2004/0249472 A1 | 12/2004 | Liu et al. | |
| 2004/0258726 A1 | 12/2004 | Stupp et al. | |
| 2004/0265780 A1 | 12/2004 | Robb et al. | |
| 2005/0008620 A1 | 1/2005 | Shimp et al. | |
| 2005/0019365 A1 | 1/2005 | Frauchiger et al. | |
| 2005/0031704 A1 | 2/2005 | Ahn | |
| 2005/0038498 A1 | 2/2005 | Dubrow et al. | |
| 2005/0084513 A1 | 4/2005 | Tang | |
| 2005/0100937 A1 | 5/2005 | Holmes | |
| 2005/0113834 A1 | 5/2005 | Breitenstien et al. | |
| 2005/0113936 A1 | 5/2005 | Brustad et al. | |
| 2005/0175670 A1 | 8/2005 | Aoyagi et al. | |
| 2005/0211680 A1 | 9/2005 | Li et al. | |
| 2005/0226939 A1 | 10/2005 | Ramalingam et al. | |
| 2005/0249654 A1 | 11/2005 | Chow | |
| 2006/0039951 A1 | 2/2006 | Sapieszko et al. | |
| 2006/0105015 A1 | 5/2006 | Perla et al. | |
| 2006/0110306 A1 | 5/2006 | Chow et al. | |
| 2006/0141002 A1 | 6/2006 | Liu et al. | |
| 2006/0178751 A1 | 8/2006 | Despres, III et al. | |
| 2006/0229715 A1 | 10/2006 | Istephanous et al. | |
| 2006/0246105 A1 | 11/2006 | Molz et al. | |
| 2006/0257358 A1 | 11/2006 | Wen et al. | |
| 2006/0257492 A1 | 11/2006 | Wen et al. | |
| 2007/0010893 A1 | 1/2007 | Wen et al. | |
| 2007/0184299 A1 | 8/2007 | Wei | |
| 2007/0190107 A1 | 8/2007 | Tosatti et al. | |
| 2008/0206554 A1 | 8/2008 | Riman et al. | |
| 2008/0213726 A1 | 9/2008 | Schlottig et al. | |
| 2009/0120457 A1 | 5/2009 | Naghshineh et al. | |
| 2009/0132048 A1 | 5/2009 | Denzer | |
| 2009/0191507 A1 | 7/2009 | Charlton et al. | |
| 2010/0136506 A1 | 6/2010 | Park | |
| 2010/0179665 A1 | 7/2010 | Schlottig et al. | |
| 2010/0260922 A1 | 10/2010 | Owens et al. | |
| 2011/0008753 A1 | 1/2011 | Rupprecht et al. | |
| 2011/0059312 A1 | 3/2011 | Howling et al. | |
| 2011/0104638 A1 | 5/2011 | Schlottig et al. | |
| 2012/0328905 A1 | 12/2012 | Guo et al. | |
| 2013/0196289 A1 | 8/2013 | Schwarz et al. | |
| 2013/0209951 A1 | 8/2013 | Piascik et al. | |
| 2016/0184059 A1 | 6/2016 | Mayfield et al. | |
| 2017/0100797 A1* | 4/2017 | Guo | B23K 26/0084 |

FOREIGN PATENT DOCUMENTS

| | | |
|---|---|---|
| CA | 2599269 A1 | 9/2006 |
| CA | 2600718 A1 | 9/2006 |
| DE | 3516411 A1 | 11/1986 |
| EP | 0450939 A2 | 10/1991 |
| EP | 0450939 B1 | 1/1997 |
| EP | 1275422 A2 | 1/2003 |

(56) References Cited

FOREIGN PATENT DOCUMENTS

| EP | 1502570 | | 2/2005 |
| GB | 2045083 | A | 10/1980 |
| JP | 0218463 | A | 1/1990 |
| JP | 05224448 | A | 9/1993 |
| WO | WO-9513101 | A1 | 5/1995 |
| WO | WO-9513102 | A1 | 5/1995 |
| WO | WO-9639202 | A1 | 12/1996 |
| WO | WO-2006096793 | A2 | 9/2006 |
| WO | WO-2006102347 | A2 | 9/2006 |
| WO | WO-2007035217 | A2 | 3/2007 |

OTHER PUBLICATIONS

"U.S. Appl. No. 13/074,670, Non Final Office Action dated Mar. 11, 2013", 8 pgs.
"U.S. Appl. No. 13/074,670, Notice of Allowance dated Oct. 10, 2013", 9 pgs.
"U.S. Appl. No. 13/074,670, Preliminary Amendment filed Mar. 11, 2013", 6 pgs.
"U.S. Appl. No. 13/074,670, Response filed Jul. 11, 2013 to Non Final Office Action dated Mar. 11, 2013", 10 pgs.
"U.S. Appl. No. 13/074,670, Response filed Oct. 2, 2013 to Final Office Action dated Aug. 6, 2013", 12 pgs.
"U.S. Appl. No. 14/049,961, Examiner Interview Summary dated Oct. 30, 2014", 3 pgs.
"U.S. Appl. No. 14/049,961, Non Final Office Action dated Sep. 17, 2014", 6 pgs.
"U.S. Appl. No. 14/049,961, Notice of Allowance dated Jan. 22, 2015", 5 pgs.
"U.S. Appl. No. 14/049,961, Preliminary Amendment filed Oct. 9, 2013", 6 pgs.
"U.S. Appl. No. 14/049,961, Preliminary Amendment filed Oct. 15, 2013", 6 pgs.
"U.S. Appl. No. 14/049,961, Response filed Dec. 10, 2014 to Non Final Office Action dated Sep. 17, 2014", 6 pgs.
"U.S. Appl. No. 14/687,625, Non Final Office Action dated Aug. 18, 2015", 7 pgs.
"U.S. Appl. No. 14/687,625, Notice of Allowance dated Nov. 9, 2015", 7 pgs.
"U.S. Appl. No. 14/687,625, Preliminary Amendment filed Apr. 15, 2015", 6 pgs.
"U.S. Appl. No. 14/687,625, Preliminary Amendment filed Apr. 21, 2015", 5 pgs.
"U.S. Appl. No. 14/687,625, Response filed Oct. 27, 2015 to Non Final Office Action dated Aug. 18, 2015", 7 pgs.
"U.S. Appl. No. 15/066,213, Non Final Office Action dated Jan. 9, 2017", 7 pgs.
"U.S. Appl. No. 15/066,213, Notice of Allowance dated May 8, 2017", 5 pgs.
"U.S. Appl. No. 15/066,213, Preliminary Amendment filed Jul. 8, 2016", 6 pgs.
"U.S. Appl. No. 15/066,213, Response filed Apr. 10, 2017 to Non Final Office Action dated Jan. 9, 2017", 6 pgs.
"International Application Serial No. PCT/US2006/044000, International Search Report dated Jul. 2, 2007", 3 pgs.
Li, et al., "Hydroxyapatite coating by dipping method and bone bonding strength", vol. 7. Materials Science Materials in Medicine, (1996), 355-357.

\* cited by examiner

TITANIUM NANO-SCALE ETCHING ON AN IMPLANT SURFACE

RELATED APPLICATION

This application claims the benefit of U.S. Provisional Application No. 61/318,641, filed Mar. 29, 2010.

FIELD OF THE INVENTION

This invention relates generally to implants and, in particular, to a dental implant having a nanometer-scale surface topography and methods of making same.

BACKGROUND OF THE INVENTION

It is becoming more common to replace a missing tooth with a prosthetic tooth that is placed upon and attached to a dental implant. Dental implants are often comprised of metal and metal alloys, including titanium (Ti) and titanium alloys. The dental implant serves as an artificial root that integrates with the gingiva and the bone tissue of the mouth.

For the dental implant to function successfully, sufficient osseointegration is required. In other words, a bond between the implant and the bone must be formed and retained. The surface of the implant may be roughened to help enhance the osseointegration process. Non-limiting examples of processes for roughening an implant surface include acid etching and grit blasting, which impart roughness on the surface.

Other existing techniques involve forming a generally thin (e.g., generally less than 10 microns) coating of osseointegration materials, such as hydroxyapatite (HA), other calcium phosphates, or other osseointegration compounds, for forming a direct chemical compound between the implant and the bone. Plasma spraying and sputtering are two major techniques that have been used to deposit, for example, HA, onto an implant.

U.S. Pat. App. Pub. Nos. 2008/0220394, 2007/0110890, and 2007/0112353 disclose methods of discrete deposition of hydroxyapatite crystals to impart a nano-scale topography. Although effective, the disclosed processes require that a residual substance (i.e. HA crystals) be left on the surface post-processing in order to impart a nano-scale topography into the surface.

The present invention is directed to an improved implant having nanometer-scale surface topography directly imparted into the surface for improving the rate and extent of osseointegration, and methods of making the same.

SUMMARY OF THE INVENTION

The present invention relates to a method of forming an implant to be implanted into living bone. The method comprises the acts of roughening at least a portion of the implant surface to produce a microscale roughened surface. The method further comprises the act of immersing the microscale roughened surface into a solution containing hydrogen peroxide and a basic solution to produce a nanoscale roughened surface consisting of nano pitting superimposed on the microscale roughened surface.

In another aspect, another method of forming an implant to be implanted into living bone is disclosed. The method comprises the act of removing a native oxide layer from at least a portion of the implant surface. The method further comprises the act of roughening at least the portion of the implant surface to produce a microscale roughened surface. The method further comprises the act of rinsing the microscale roughened surface in deionized water. The method further describes the act of immersing the microscale roughened surface into a solution containing hydrogen peroxide and a basic solution at a high pH level to produce a nanoscale roughened surface consisting of nano-pitting superimposed on the microscale roughened surface. The method further comprises the acts of passivating the nanoscale roughened surface with nitric acid, and rinsing the nanoscale roughened surface in deionized water.

The above summary of the present invention is not intended to represent each embodiment, or every aspect, of the present invention. This is the purpose of the figures and the detailed description which follow.

BRIEF DESCRIPTION OF THE DRAWINGS

The foregoing and other advantages of the invention will become apparent upon reading the following detailed description and upon reference to the drawings.

DETAILED DESCRIPTION OF THE INVENTION

The present invention is directed to implants having a nanometer scale surface topography consisting of irregular shaped pitting and methods of making the same. An implant in the context of the present invention means a device intended to be placed within a human body such as to connect skeletal structures (e.g., a hip implant) or to serve as a fixture for a body part (e.g., a fixture for an artificial tooth).

Although the remainder of this application is directed to a dental implant, it is contemplated that the present invention may also be applied to other (e.g., medical) implants.

Figure 1:
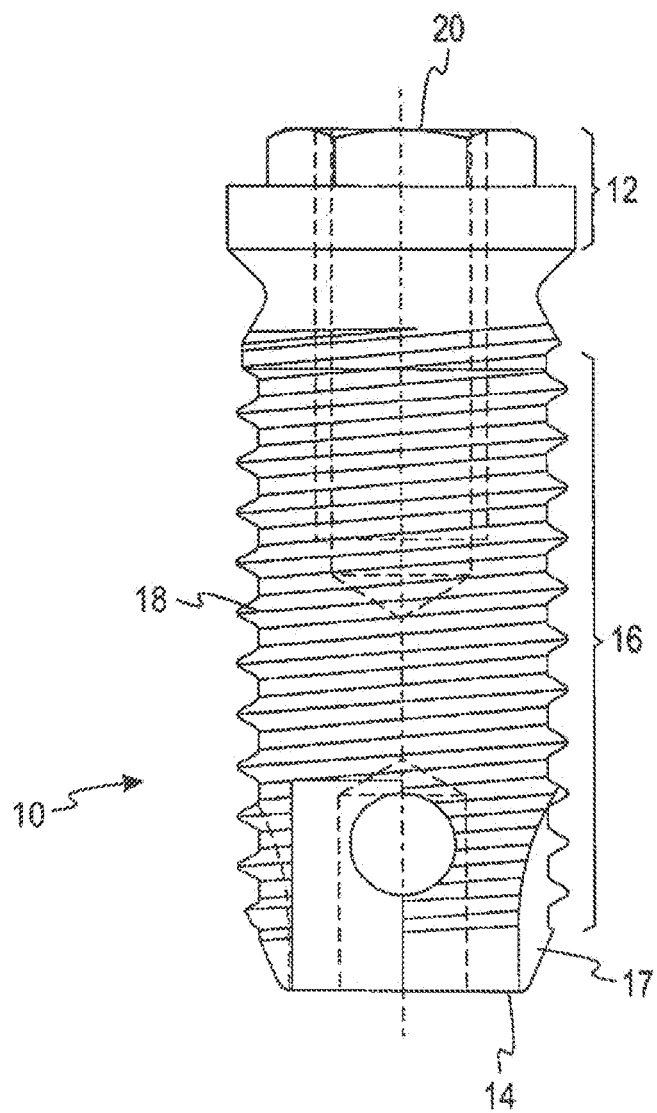
FIG. 1 is a side view of an implant according to one embodiment.

FIG. 1 shows a standard dental implant 10 that includes an head portion 12, a lowermost end 14, and a threaded bottom portion 16. The implant 10 may, for example, be made of titanium, tantalum, cobalt, chromium, stainless steel, or alloys thereof. FIGS. 2a-c, 3a-c, and 4a-b, which are discussed below, describe alternative implant designs that may also be used with the present invention.

In the implant 10 of FIG. 1, the head portion 12 includes a non-rotational feature. In the embodiment shown, the non-rotational feature includes a polygonal boss 20 that may be engageable with a tool that screws the implant 10 into bone tissue. In the illustrated embodiment, the polygonal boss 20 is hexagonal. The polygonal boss 20 may also be used for non-rotationally engaging a correspondingly shaped socket on a restorative or prosthetic component that is attached to the implant 10.

The exterior of the threaded bottom portion 16 facilitates bonding with bone or gingiva. The threaded bottom section 16 includes a thread 18 that makes a plurality of turns around the implant 10. The threaded bottom portion 16 may further include a self-tap pin region with incremental cutting edges 17 that allows the implant 10 to be installed without the need for a bone tap. These incremental cutting edges 17 are described in detail in U.S. Pat. No. 5,727,943, entitled "Self-Tapping, Screw-Type Dental Implant," which is incorporated by reference in its entirety.

Figure 2B:
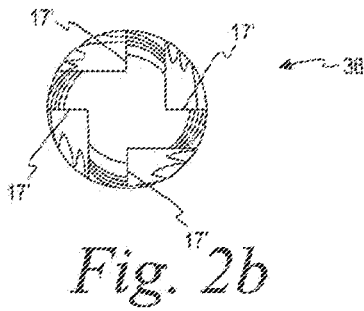
FIGS. 2a, 2b, and 2c, are a side view, an insertion end view, and a gingival end view, respectively, of an implant according to a second embodiment.
Figure 2A:
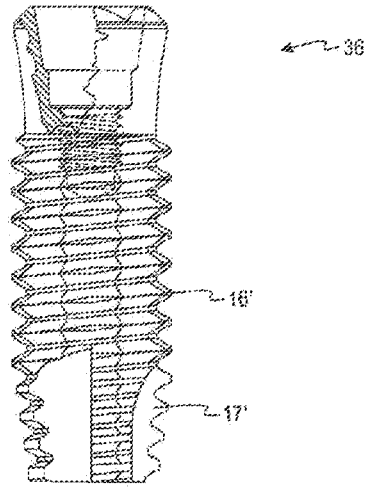
Figure 2C:
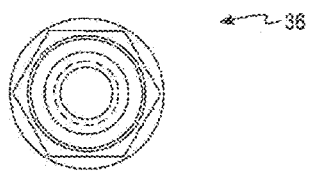

FIGS. 2a-c disclose an implant 36 that differs from the implant 10 of FIG. 1 in the details of the cutting edges 17' and the contours of the threads defining the exterior of the threaded bottom portion 16'. When viewed in the cross-section (see FIG. 1b), the threaded outer surface 16' is non-circular in the region of the threads and/or the troughs between the threads. This type of thread structure is described in detail in U.S. Pat. No. 5,902,109, entitled "Reduced Friction, Screw-Type Dental Implant," which is incorporated by reference in its entirety.

Figure 3B:
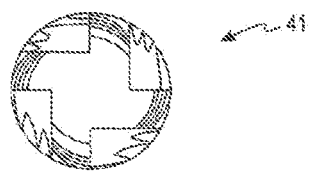
FIGS. 3a, 3b, and 3c, are a side view, an insertion end view, and a gingival end view, respectively, of an implant according to third embodiment.
Figure 3A:
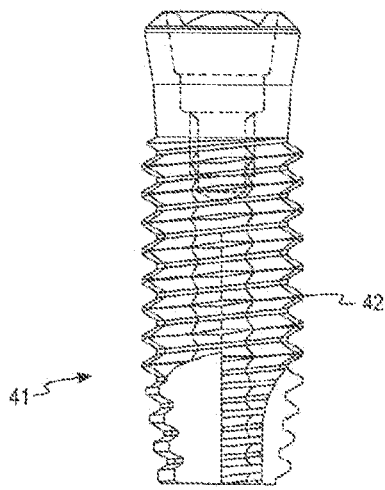
Figure 3C:
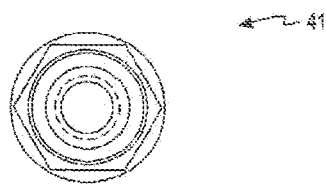

In FIGS. 3a-c, an implant 41 having a wide diameter in the region of the threaded bottom portion 42 is illustrated. The diameter is in the range of from about 4.5 mm to about 6.0 mm with the diameter of 5.0 mm being a fairly common dimension for a wide diameter implant. Such an implant 41 is useful to engage one or both cortical bones to provide enhanced stability, especially during the period of time after installation.

Figure 4B:
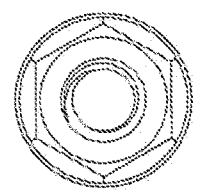
FIGS. 4a and 4b are a side view, an end view, and a cross-sectional view, respectively, of an implant according to a fourth embodiment.
Figure 4A:
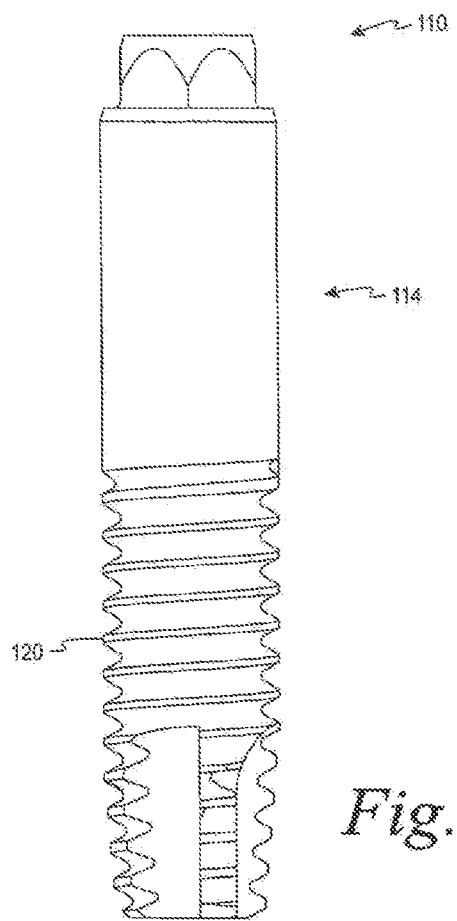

FIGS. 4a-b illustrate an implant 110 according to another embodiment that may be used with the present invention. The implant 110 includes a middle section 114 designed to extend through the gingiva. Preferably, it is a smooth surface that includes a titanium nitride coating so the underlying titanium or titanium alloy is not readily seen through the gingiva. The implant 110 also includes a threaded portion 120 that may include various thread structures and is preferably roughened to increase the osseointegration process. It is contemplated that implants other than those illustrated in FIGS. 1-4 may be used with the present invention.

According to embodiments of the present invention, a nanoscale roughened surface is superimposed onto a microscale roughened surface on at least a portion (e.g., the threaded bottom portion) of the surface of an implant. In one embodiment, the nanoscale roughened surface is created by immersing the microscale roughened surface into a solution containing hydrogen peroxide and a basic solution. Non-limiting examples of suitable basic solutions include potassium hydroxide solutions and sodium hydroxide solutions.

Figure 5:
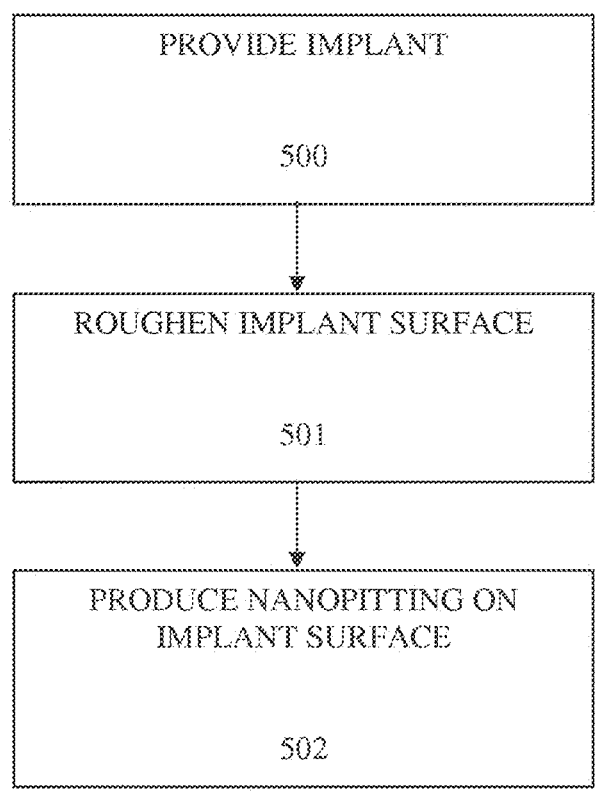
FIG. 5 is a flow diagram detailing a method of forming an implant according to an embodiment of the present invention.
Figure 6:
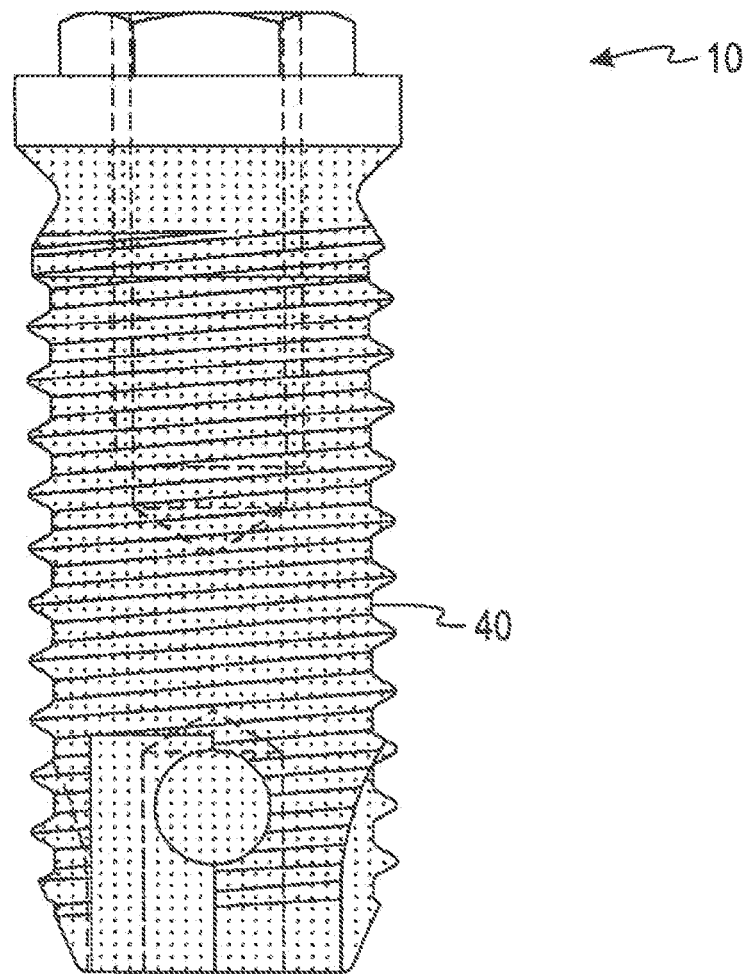
FIG. 6 is a side view of the implant in FIG. 1 with a roughened outer surface.

Turning now to FIG. 5, a general method of producing a nanoscale roughened surface on an implant is set forth according to one embodiment of the present invention. At step 500, an implant is provided. At least a portion of the implant surface is roughened to a microscale roughness at step 501, for example, by machining, acid etching and/or grit blasting the implant surface. As an example, FIG. 6 shows the implant 10 of FIG. 1 having a roughened surface 630. Nanopitting is then created on the microscale roughened surface by immersion into a solution containing hydrogen peroxide and a basic solution, to produce a nanoscale roughened surface on the implant at step 502.

Figure 7A:
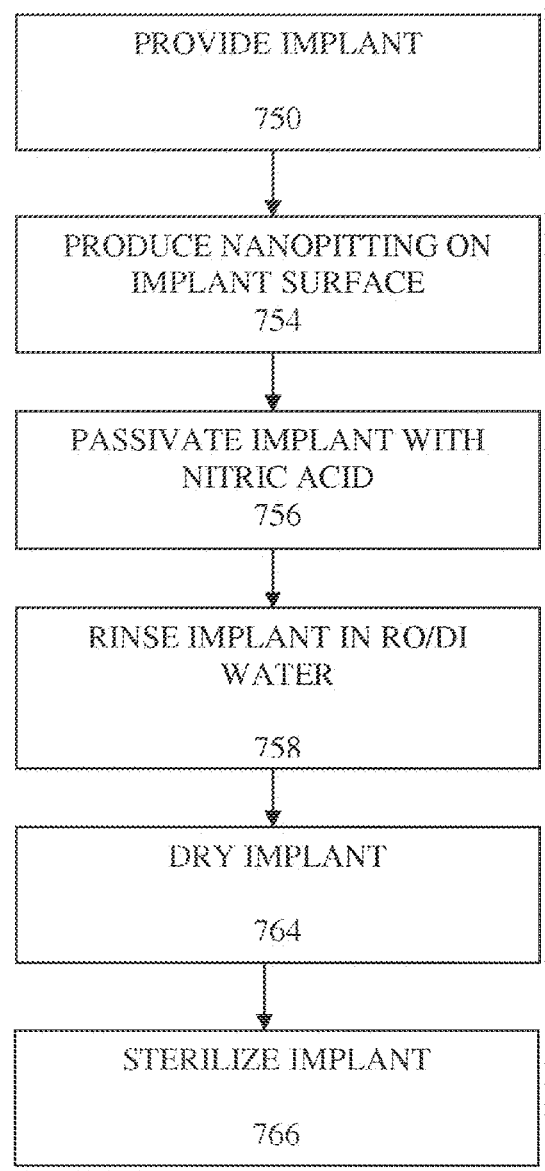
FIG. 7a is a flow diagram detailing a method of forming an implant according to another embodiment of the present invention.

Referring now to FIG. 7a, another general method of forming an implant according to another embodiment of the present invention is illustrated. An implant comprised of titanium, a titanium alloy (e.g. titanium 6AL-4V ELI alloy), stainless steel, or the like is provided at step 750. At step 754, nanopitting is created on a microscale roughened surface to produce a nanoscale roughened surface on the implant. At step 756, the implant is passivated with nitric acid. The implant may then be rinsed in reverse osmosis/deionized (RO/DI) water to remove residual solvents and hydroxyapatite at step 758. The implant is then dried at step 764 and sterilized at step 766 using, for example, gamma sterilization techniques.

Figure 7B:
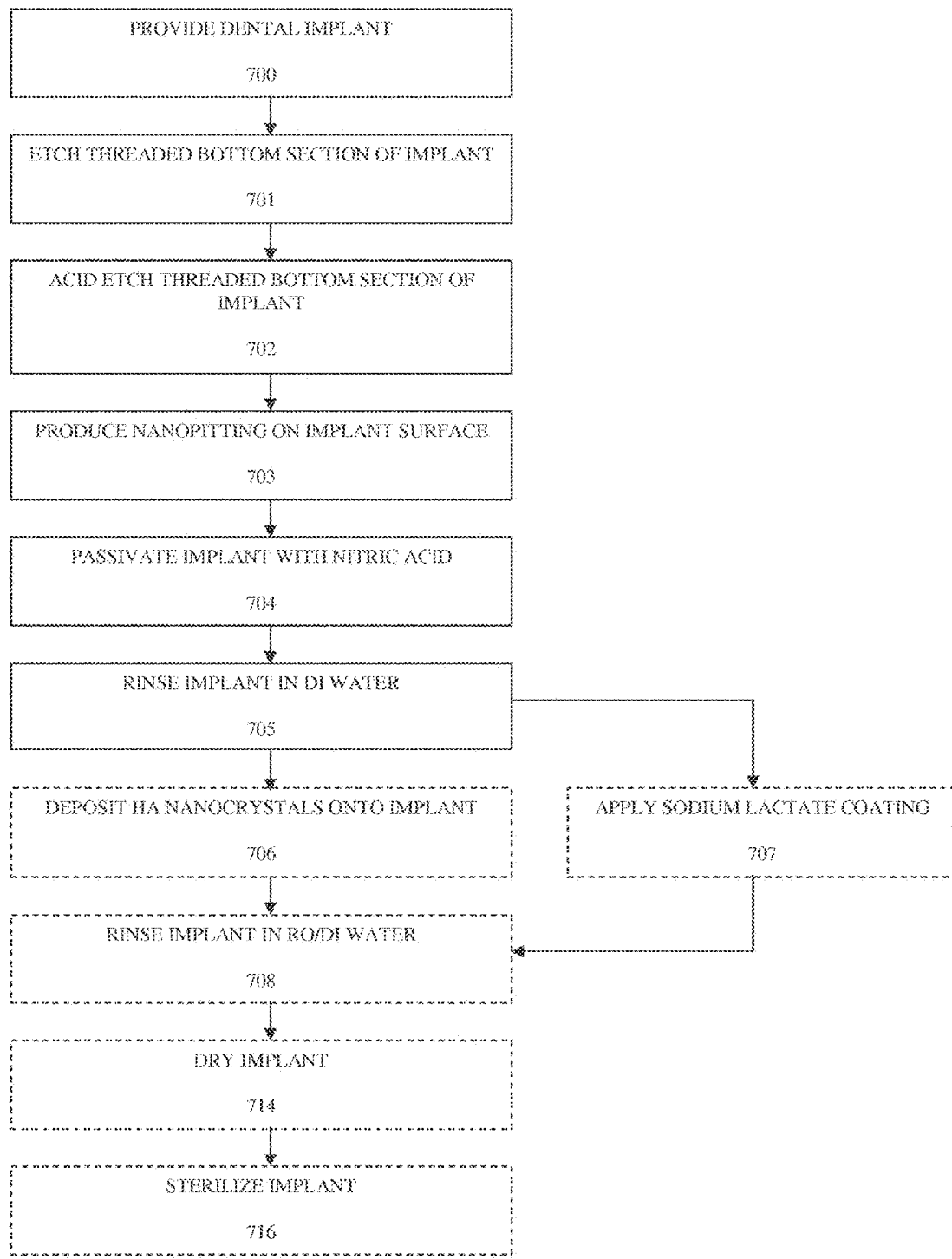
FIG. 7b is a flow diagram detailing a method of forming an implant according to yet another embodiment of the present invention.

Referring to FIG. 7b, a more detailed method of producing a nanoscale roughened surface on an implant is illustrated according to another embodiment of the present invention. A threaded dental implant comprised of titanium, a titanium alloy (e.g., titanium 6AL-4V ELI alloy), stainless steel, or the like is provided at step 700. The surface of the implant is generally clean and dry. A threaded bottom portion of the implant is etched to remove a native oxide layer from the implant surface at step 701. The native oxide layer may be removed by a first acid solution, which may include aqueous hydrofluoric acid. The threaded bottom portion is then acid etched form a microscale roughened surface at step 702. "Microscale," as used herein, should be understood to describe an article or feature generally measured in microns such as, for example, 1 micron to 100 microns. Acid etching may result from immersion in a mixture of sulfuric and hydrochloric acids, creating peak-to-peak and peak-to-valley irregularity distances in the microscale roughened surface of about 1 micron to 3 microns. This type of roughening method utilized on commercially pure (CP) titanium is described in detail in U.S. Pat. No. 5,876,453, entitled "Implant Surface Preparation," which is incorporated by reference in its entirety. An additional roughening method utilized on Titanium 6AL-4V ELI alloy is described in detail in U.S. Pat. App. Pub. No. 2004/0265780, entitled "Surface Treatment Process for Implants Made of Titanium Alloy," which is also incorporated by reference in its entirety. It is contemplated that other surface roughening techniques including, but not limited to, grit blasting, titanium plasma spraying, and combinations thereof, may be used. Grit blasting the threaded bottom portion to form a microscale roughened surface generally results in peak-to-peak and peak-to-valley irregularity distances of about 10 microns to 30 microns. Grit blasting and acid etching the threaded bottom portion to form the microscale roughened surface generally results in both levels of topographies, i.e., with about 1 micron to 3 microns peak-to-peak and peak-to-valley irregularity distances superimposed on 10 microns to 30 microns peak-to-peak and peak-to-valley irregularity distances on the microscale roughened surface.

At step 703, the microscale roughened surface is immersed into a solution containing hydrogen peroxide and a basic solution to produce a nanoscale roughened surface consisting of nanopitting superimposed on the microscale roughened surface. The basic solution can be any base with a pH in the range of about 7 to about 14, and preferably about 14, such as potassium hydroxide or sodium hydroxide. "Nanoscale," as used herein, should be understood to describe an article or feature generally measured in nanometers such as, for example, 1 nanometer to 500 nanometers. Generally, immersion into the hydrogen peroxide/basic solution results in nanopitting of about 1 nanometer to about 100 nanometers.

Immersion time, hydrogen peroxide concentration, and basic solution concentration are among several factors that affect the rate and amount of nanopitting superimposed onto the microscale roughness of the implant surface. For example, immersing a commercially pure titanium implant in a solution of 3-5% potassium hydroxide and 13-22% hydrogen peroxide for 1 minute at 50 degrees Celsius typically results in an acceptable nanoscale roughness of the implant surface. Longer immersion times may impact the micron level topographies, while potassium hydroxide concentrations of less than 3% and/or hydrogen peroxide concentrations of less than 13% may result in the nano-topography not being adequately formed.

Another factor affecting the rate and amount of nanopitting onto the microscale roughness of the implant surface is the processing temperature. At temperatures of higher than about 60 degrees Celsius, for example, the etching is accelerated and can begin to impact the micron level topographies. Thus, it may be desirable for the processing temperature to be maintained at or below about 60 degrees Celsius.

Processing temperature, immersion time, and/or chemical concentration may be adjusted to compensate for one or more of these variables being within an otherwise unacceptable range, in order to nevertheless produce acceptable nano-topography. For example, potassium hydroxide concentrations of less than 3% may be adjusted by increasing immersion time and/or processing temperature in order to produce an acceptable amount of nanopitting on the microscale roughness of the implant surface.

Post-processing, the implant is passivated with nitric acid at step 704. At step 705, the implant is rinsed in hot do ionized water (e.g. 70 degrees Celsius to 100 degrees Celsius) to remove any acid residuals and to potentially enhance titanium hydroxide groups on the surface.

Hydroxyapatite (HA) nanocrystals may then optionally be deposited on the nanoscale roughened surface of the implant at step 706. The HA nanocrystals may be introduced onto the nanoscale roughened surface of the implant in the form of a colloid. A representative amount of HA in the colloid is typically in the range of about 0.01 weight percent to about 1 weight percent (e.g., 0.10 weight percent). To form the colloid, HA nanocrystals may be combined in solution with a 2-methoxyethanol solvent and ultrasonically dispersed and deagglomerated. The pH of the colloidal solution may be adjusted with sodium hydroxide, ammonium hydroxide, or the like on the other of about 7 to about 13. As such, the colloidal solution may include HA nanocrystals, 2-methoxyethanol, and a pH adjuster (e.g. ammonium hydroxide, and/or sodium hydroxide). This type of HA deposition is described in detail in U.S. Pat. App. Pub. Nos. 2007/0110890 and 2007/01112353, both entitled "Deposition of Discrete Nanoparticles on an Implant Surface," which are incorporated by reference in their entireties. The implant may then be rinsed in reverse osmosis/deionized (RO/DI) water to remove residual solvent and HA at step 708.

Alternatively or in addition to the acts of depositing HA nanocrystals at step 706 and rinsing at step 708, a sodium lactate coating may be applied on the nanoscale roughened surface of the implant at step 707 and the implant rinsed at step 708. In either embodiment, the implant may then be dried (e.g., oven dried), at step 714, and sterilized at step 716 using, for example, gamma sterilization.

The implant surface may be characterized utilizing Field Emission Scanning Electron microscopy (FESEM). Depending upon the resolution of the instrument, the nanopitting may typically be witnessed at magnifications of 30kX or higher. As discussed above, the nanopitting generally has a distribution in the range of about 1 nanometer to about 500 nanometers, and typically between about 1 nanometer and about 100 nanometers.

EXAMPLE 1

Figure 8A:
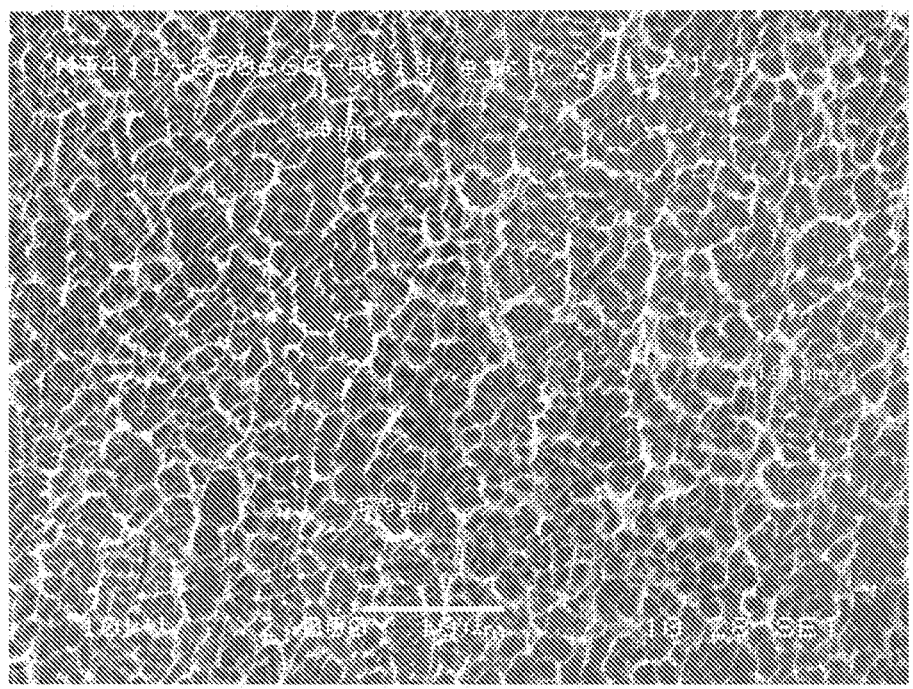
FIG. 8a is a scanning electron microscope (SEMI) image showing a commercially pure titanium implant post-acid etching at 2kX.
Figure 8B:
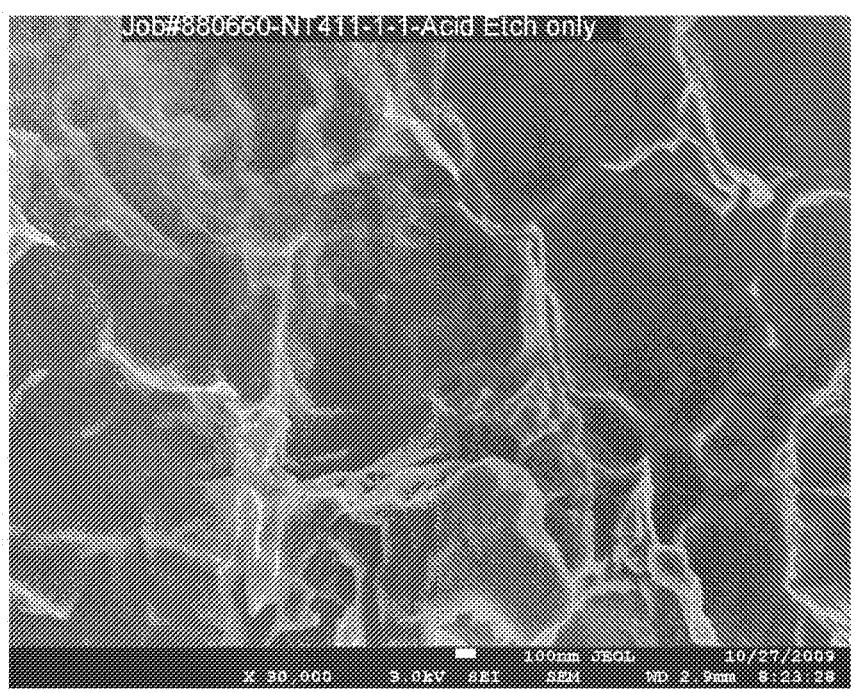
FIG. 8b is a field emission scanning electron microscope (FESEM) image showing a commercially pure titanium implant post-acid etching at 30kX.

FIGS. 8a and 8b are scanning electron microscope images showing a micron-level roughness imparted by an acid etching process on a commercially pure titanium implant. The image of FIG. 8a was taken at 2kX utilizing an SEM. The image of FIG. 8b was taken at 30kX utilizing an FESEM.

The implant shown in FIGS. 8a and 8b was machined, cleaned, and acid etched to impart a microscale roughness on the surface of the implant using a process similar to that described in U.S. Pat. No. 5,603,338, herein incorporated by reference in its entirety. The native oxide layer of the implant was removed via immersion in a hydrofluoric acid solution of about 5% v/v (about 8.5% w/w) for about 60 seconds at about 20-25 degrees Celsius. The acid etching was accomplished by immersion in an $H_2SO_4$/HCl solution for about 7 minutes at about 60-70 degrees Celsius. FIG. 8a demonstrates the micron-level topography imparted by this acid etching at a magnification of 2kX. Characteristic 1-3 micron peak-to-peak micropitting is clearly defined. FIG. 8b, which is an FESEM image of the surface at a magnification of 30kX, demonstrates the general lack of nanometer-scale surface roughness features after this level of processing.

The implant was then immersed in about 4% w/w potassium hydroxide and about 16% w/w hydrogen peroxide at a starting temperature of about 50 degrees Celsius for about 1 minute, according to one embodiment of the invention. Post-processing, the implant was thoroughly rinsed in de-ionized water, then passivated through 40 kHz ultrasonic immersion in about 22% w/w nitric acid for about 10 minutes at about 60 degrees Celsius, followed by additional rinsing in de-ionized water, and oven drying at about 100-150 degrees Celsius.

Figure 9A:
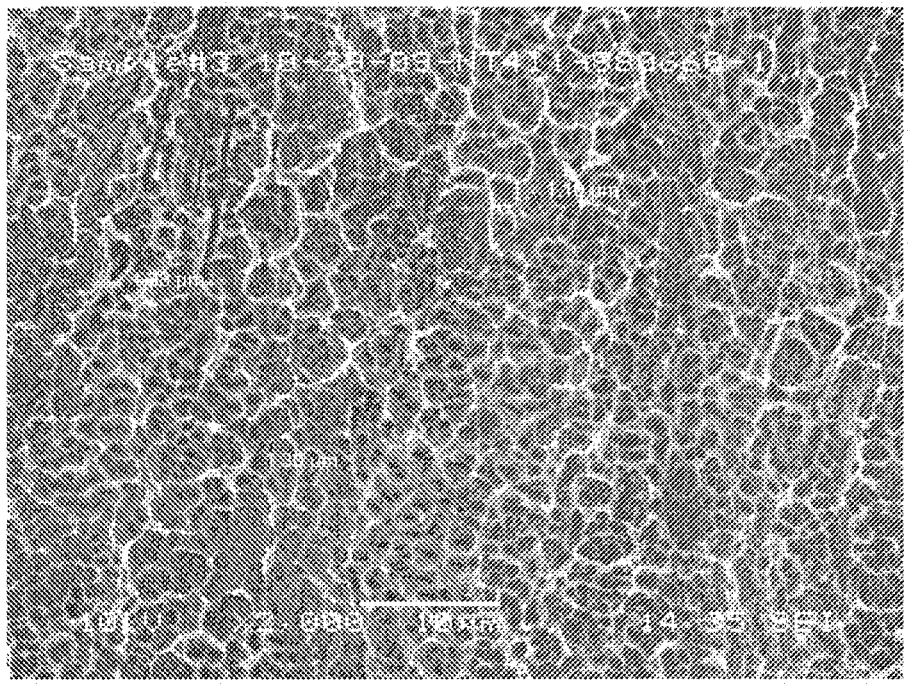
FIG. 9a is an FESEM image showing a commercially pure titanium implant post-KOH/$H_2O_2$ treatment at 2kX using a method of the present invention.
Figure 9B:
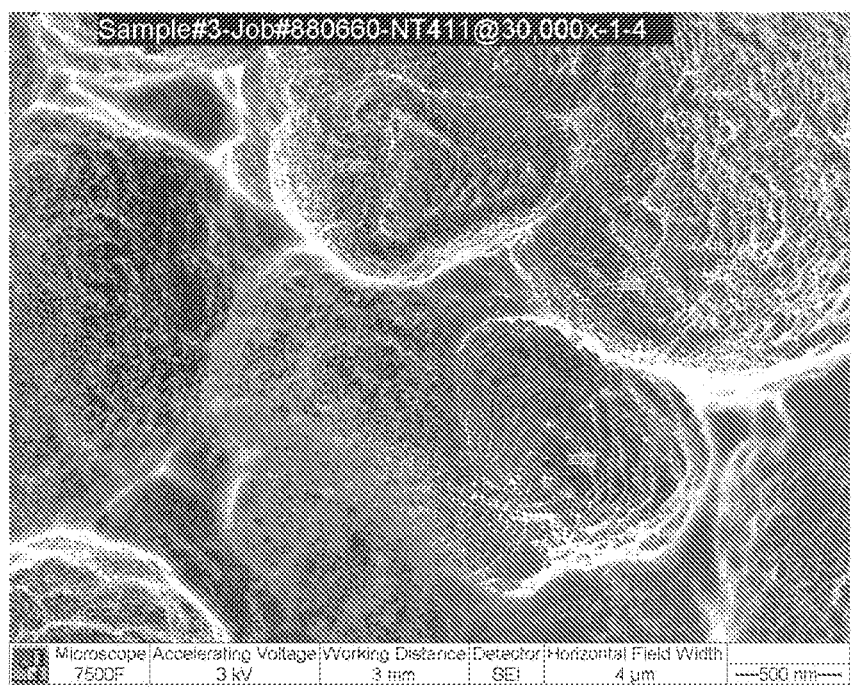
FIG. 9b is an FESEM image showing a commercially pure titanium implant post-KOH/$H_2O_2$ treatment at 30kX using a method of the present invention.
Figure 9C:
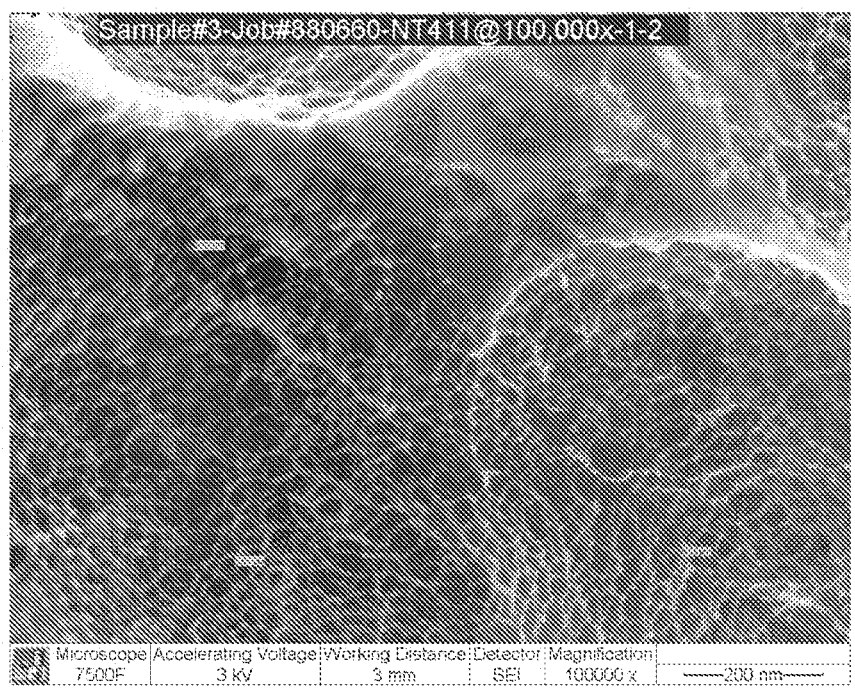
FIG. 9c is an FESEM image showing a commercially pure titanium implant post-KOH/$H_2O_2$ treatment at 100kX using a method of the present invention.

The additional processing imparted a nanometer level topography, as demonstrated in the FESEM images of FIGS. 9a-c. FIG. 9a, which is an FESEM image at a magnification of 2kX, demonstrates the micron-level roughness imparted by the acid etching remains on the implant, including the characteristic 1-3 micron peak-to-peak micropitting. The nanoscale roughness cannot be witnessed at this iriagnification.

FIG. 9b, which shows the surface of FIG. 9a at a magnification of 30kX, demonstrates the nanoscale roughness features of the implant surface. Nanopitting in the 1-100 nanometer range can be witnessed at this magnification. FIG. 9c, which is a magnification of the surface of FIGS. 9a and 9b at 100kX, more clearly demonstrates the resultant nanoscale roughness.

The implant shown in FIGS. 9a-c was then evaluated for surface chemistry utilizing Electron Dispersion Spectroscopy. A spot size of approximately 275×375 microns was analyzed for chemistry. The freshly processed and passivated sample demonstrated a 100% titanium surface chemistry, indicating that no residuals were present at the detection limit of the nstrument.

EXAMPLE 2

All of the solutions containing the concentrations of KOH and $H_2O_2$ provided in Table 1 below resulted in acceptable nano-topography on commercially pure titanium with about 1 minute exposure to a hydrogen peroxide and potassium hydroxide solution at about 50 degrees Celsius:

TABLE 1

| Concentrations of KOH and $H_2O_2$ | |
|---|---|
| % KOH | % $H_2O_2$ |
| 4 | 16 |
| 4 | 19 |
| 4 | 22 |
| 3 | 16 |
| 3 | 19 |
| 5 | 13 |
| 5 | 19 |

A solution having about 4% w/w KOH and about 16% w/w $H_2O_2$ resulted in acceptable nano-topography on titanium 6AL-4V ELI with 1 minute exposure to a hydrogen peroxide and potassium hydroxide solution at about 50 degrees Celsius.

A solution having about 4% w/w NaOH and about 16% w/w $H_2O_2$ resulted in acceptable nano-topography on titanium 6AL-4V ELI with about 1 minute exposure to a hydrogen peroxide and sodium hydroxide solution at about 50 degrees Celsius.

EXAMPLE 3

All of the solutions containing the concentrations of KOH and $H_2O_2$ provided in Table 2 below, with KOH and $H_2O_2$ concentrations ranging from about 1% w/w to about 6% w/w resulted in acceptable nano-topography on grit-blasted and acid-etched commercially pure titanium with about 4 minute exposure to a hydrogen peroxide and potassium hydroxide solution at about 33 degrees Celsius.

TABLE 2

| Concentrations of KOH and $H_2O_2$ | |
|---|---|
| % KOH | % $H_2O_2$ |
| 4 | 1 |
| 4 | 2 |
| 4 | 3 |
| 4 | 4 |
| 4 | 5 |
| 4 | 6 |
| 1 | 4 |
| 2 | 4 |
| 3 | 4 |
| 5 | 4 |
| 6 | 4 |

The solutions containing the concentrations of KOH and $H_2O_2$ provided in Table 2 slow down the method of forming acceptable nano-topography, thus improving process control in the production environment. As the base or peroxide concentration approached 0% w/w, the desired surface topography was not formed.

It is contemplated that various combinations of variables concentration of basic solution, concentration of hydrogen peroxide, exposure times, temperatures) may be used to forms the desired surface attributes. According to one non-limiting example, the desired surface may be obtained using 4.1% KOH, 3.85% $H_2O_2$, 3 minute exposure time, and 31 degrees Celsius.

While the present invention has been generally described relative to the part of the implant contacting bone tissue, it is contemplated that the acts of etching, acid etching, roughening, nanopitting, and depositing herein described may be performed on the entire implant.

While the present invention has been described with reference to one or more particular embodiments, those skilled in the art will recognize that many changes may be made thereto without departing from the spirit and scope of the present invention. Each of these embodiments and obvious variations thereof is contemplated as falling within the spirit and scope of the claimed invention, which is set forth in the following claims.

What is claimed is:

1. A method of forming an implant to be implanted into living bone, the method comprising the acts of:
   roughening at least a portion of the implant surface to produce a microscale roughened surface; and
   immersing the microscale roughened surface into a solution containing hydrogen peroxide and a basic solution to produce a nanoscale roughened surface consisting of nanopitting superimposed on the microscale roughened surface.

2. The method of claim 1, wherein the implant is made of a metal selected from the group consisting of tantalum, cobalt, chromium, titanium, stainless steel, or alloys thereof.

3. The method of claim 1, wherein the implant is a dental implant.

4. The method of claim 3, wherein the portion of the implant surface is a threaded bottom portion for facilitating bonding with bone.

5. The method of claim 1, wherein the implant is made of titanium and the act of roughening the implant surface comprises grit blasting the surface.

6. The method of claim 1, wherein the implant is made of titanium and the act of roughening the implant surface comprises:
   removing a native oxide layer from the implant surface; and
   acid etching the resulting surface.

7. The method of claim 6, wherein the act of roughening the implant surface comprises acid etching the implant surface with a solution containing sulfuric acid and hydrochloric acid.

8. The method of claim 1, wherein the basic solution is a sodium hydroxide solution.

9. The method of claim 1, wherein the basic solution is a potassium hydroxide solution.

10. The method of claim 9, wherein the potassium hydroxide solution has a concentration of about 3-5% w/w and the hydrogen peroxide has a concentration of about 13-22% w/w.

11. The method of claim 9, wherein the potassium hydroxide solution has a concentration of about 1-6% w/w and the hydrogen peroxide has a concentration of about 1-6% w/w.

12. The method of claim 1, wherein the basic solution has a pH between about 7 to about 14.

13. The method of claim 1, wherein the nanopitting is in the 1-100 nanometer range.

14. The method of claim 1, further comprising the acts of:
rinsing the nanoscale roughened surface in deionized water;
passivating the nanoscale roughened surface with nitric acid;
re-rinsing the nanoscale roughened surface in deionized water; and
drying the nanoscale roughened surface.

15. The method of claim 14, further comprising the act of sterilizing the implant.

16. The method of claim 1, further comprising the act of depositing discrete nanoparticles on the nanoscale roughened surface.

17. The method of claim 1, further comprising the act of applying a sodium lactate coating on the nanoscale roughened surface.

18. The method of claim 1, wherein the act of roughening the implant surface produces irregularities with peak-to-valley heights of less than about 10 microns and peak-to-peak distances of less than about 3 microns.

19. A method of forming an implant to be implanted into living bone, the method comprising the acts of:
removing a native oxide layer from at least a portion of the implant surface;
roughening at least the portion of the implant surface to produce a microscale roughened surface;
rinsing the microscale roughened surface in deionized water;
immersing the microscale roughened surface into a solution containing hydrogen peroxide and a basic solution at a high pH level to produce a nanoscale roughened surface consisting of nanopitting superimposed on the microscale roughened surface;
passivating the nanoscale roughened surface with nitric acid; and
rinsing the nanoscale roughened surface in deionized water.

20. The method of claim 19, wherein the act of roughening the implant surface comprises grit blasting the implant surface.

* * * * *